(12) United States Patent
Battaglia et al.

(10) Patent No.: US 6,768,012 B2
(45) Date of Patent: Jul. 27, 2004

(54) PROCESS FOR THE PREPARATION OF PACLITAXEL

(75) Inventors: Arturo Battaglia, Bologna (IT); Paolo Dambruoso, Putignano (IT); Andrea Guerrini, Bologna (IT); Ezio Bombardelli, Milan (IT); Alessandro Pontiroli, Milan (IT)

(73) Assignee: Indena S.p.A., Milan (IT)

( * ) Notice: Subject to any disclaimer, the term of this patent is extended or adjusted under 35 U.S.C. 154(b) by 0 days.

(21) Appl. No.: 10/433,601

(22) PCT Filed: Dec. 3, 2001

(86) PCT No.: PCT/EP01/14084

§ 371 (c)(1),
(2), (4) Date: Jun. 5, 2003

(87) PCT Pub. No.: WO02/46177

PCT Pub. Date: Jun. 13, 2002

(65) Prior Publication Data

US 2004/0049060 A1 Mar. 11, 2004

(30) Foreign Application Priority Data

Dec. 6, 2000 (IT) .................................... MI2000A2654

(51) Int. Cl.[7] .............................................. C07D 305/14
(52) U.S. Cl. ........................ 549/510; 549/511; 549/514
(58) Field of Search ................................. 549/510, 511, 549/514

(56) References Cited

U.S. PATENT DOCUMENTS

| 5,917,062 A | 6/1999 | Bombardelli | 549/510 |
| 6,020,507 A | 2/2000 | Gibson | 549/510 |
| 6,706,896 B1 * | 3/2004 | Holton et al. | 549/214 |

* cited by examiner

*Primary Examiner*—Rita Desai
*Assistant Examiner*—Raymond Covington
(74) *Attorney, Agent, or Firm*—Young & Thompson

(57) ABSTRACT

A process for the preparation of paclitaxel starting from 10-deacetylbaccatine III.

9 Claims, No Drawings

PROCESS FOR THE PREPARATION OF PACLITAXEL

The present invention relates to a process for the preparation of Paclitaxel.

Paclitaxel is a molecule of natural origin having wide spectrum antitumor activity, with the following structural formula:

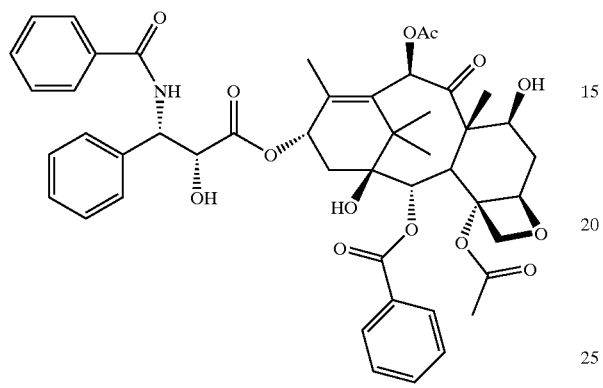

The compound, first recovered from Taxus brevifolia bark and from other natural sources, can be prepared semi-synthetically according to a number of procedures described in both scientific and patent literature.

U.S. Pat. No. 4,924,011 discloses the semi-synthesis of paclitaxel using 10-deacetylbaccatine III protected at the C-7 hydroxyl with a trialkylsilyl group and subsequently acetylated at C-10. The resulting intermediate is reacted with (2R,3S)-N-benzoyl-2-O-(1-ethoxyethyl)-3-phenyl-isoserine and the resulting product is deprotected to give paclitaxel.

WO-93/06094 discloses the preparation of paclitaxel by reacting a β-lactam precursor with 7-O-triethylsilyl-baccatine III, followed by mild acid hydrolysis.

According to U.S. Pat No. 5,476,954, paclitaxel is prepared starting from 10-deacetylbaccatine III esterified at C-7 with a 2,2,2-trichloroethoxycarbonyl group (TROC).

According to U.S. Pat. Nos. 5,917,062 and 6,020,507, the C-7 hydroxyl is protected with carbobenzoxy (CBZ) or with carbo-t-butoxy (Boc), followed by selective acetylation of C-10 hydroxyl, It is apparent from literature that a crucial aspect of paclitaxel semi-synthesis is to selectively protect the hydroxyls on the diterpen moiety (10-deacetylbaccatine III skeleton). The C-7 position is the most reactive and is therefore functionalized with groups which are easy to remove subsequently. The most commonly used group is triethylsilyl (TES), which is stable under the conditions used for the esterification of the other hydroxyls involved in the synthesis, and provides about 85% conversion yield. Approximately 85% yields are obtained when an acetyl group is subsequently introduced at the C-10 position.

A novel process for the synthesis of paclitaxel has now been found, which provides higher final yields as well as other advantages compared with the known processes.

The process according to the invention comprises the following steps:

a) protection of the hydroxyls at the 7- and 10-positions of 10-deacetylbaccatine III (10-DAB III),

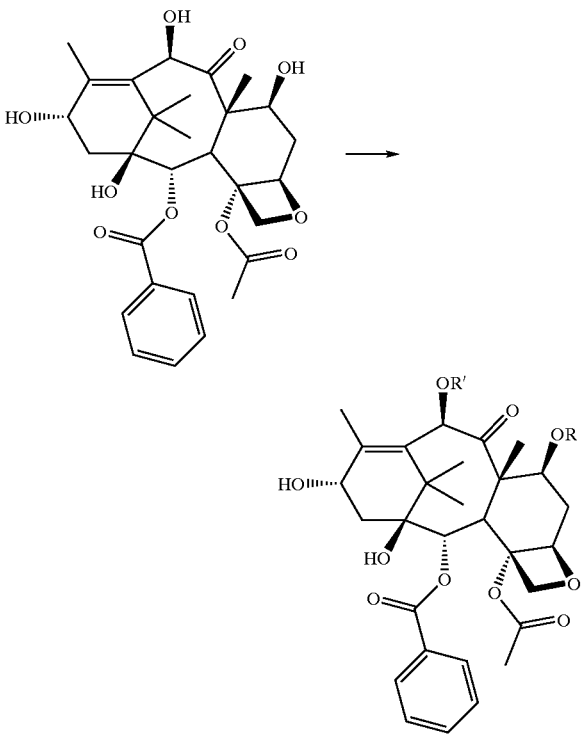

wherein R=R'=trichloroacetyl, or R'=acetyl and R is selected from t-butoxycarbonyl and trichloroacetyl, b) esterification of the hydroxyl at 13 with 3-phenyl-2-epoxypropionic acid

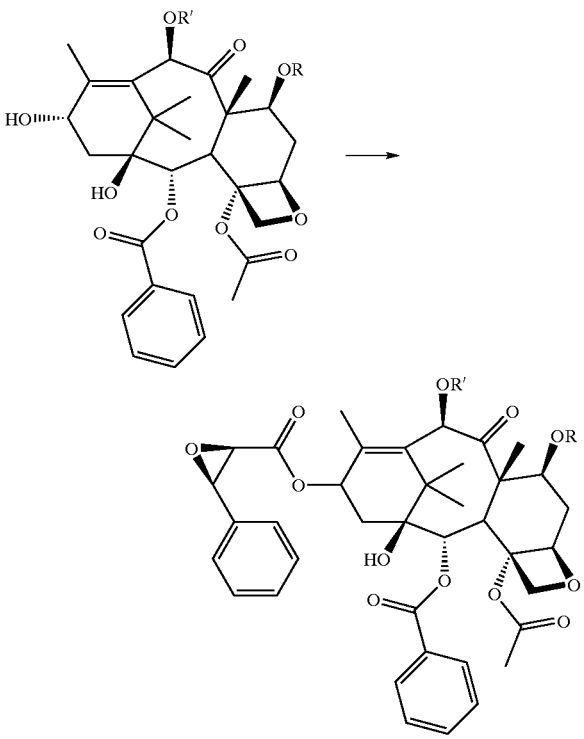

c) removal of the protective groups at the 7- and 10-positions (1) if they are both tichloroacetyl groups, followed by selective acetylation at the 10-position (2) and opening of the epoxide with sodium azide (3);

or, alternatively, c') if R'=acetyl and R=trichloroacetyl, opening of the epoxide with sodium azide and simultaneous deprotection at the 7-position

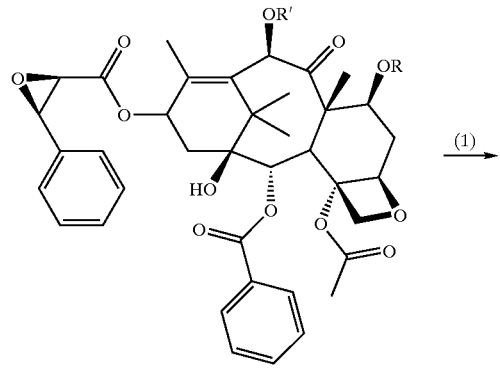

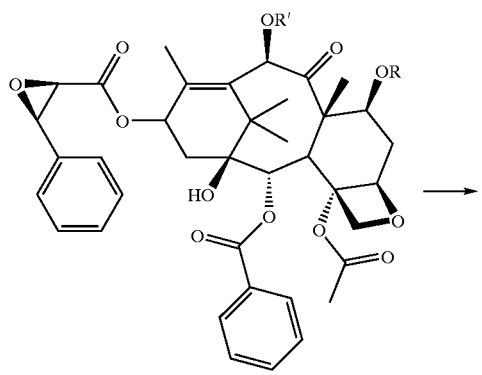

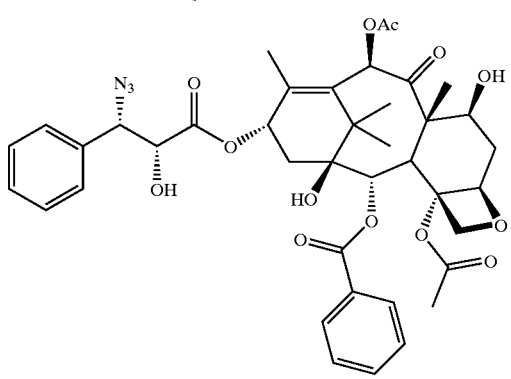

d) reduction of the azido group to amino group

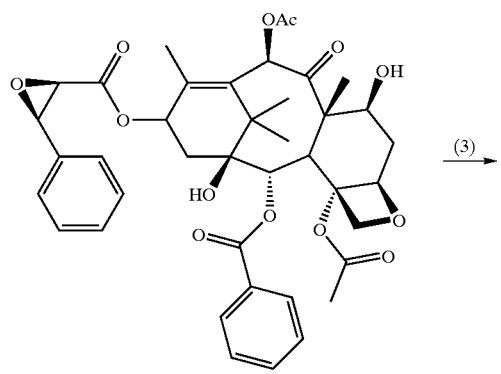

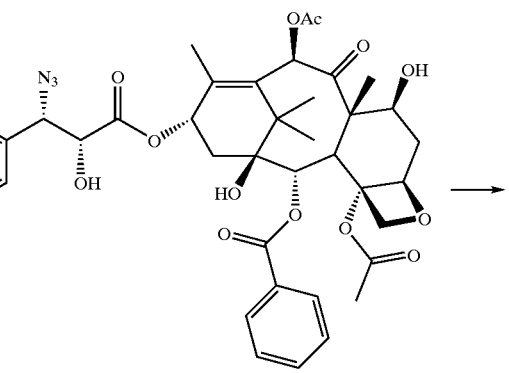

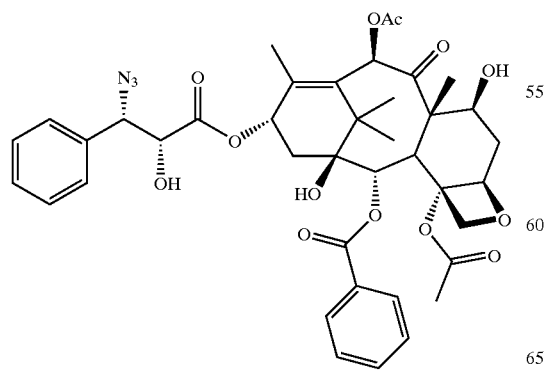

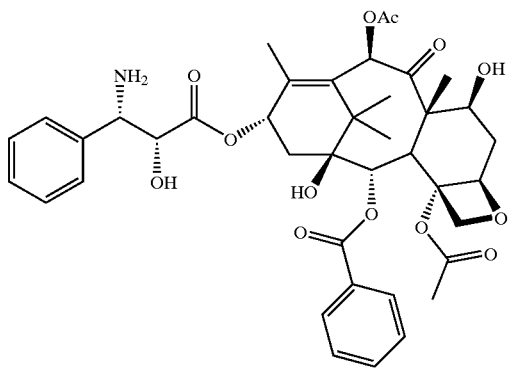

e) benzoylation to give the final product

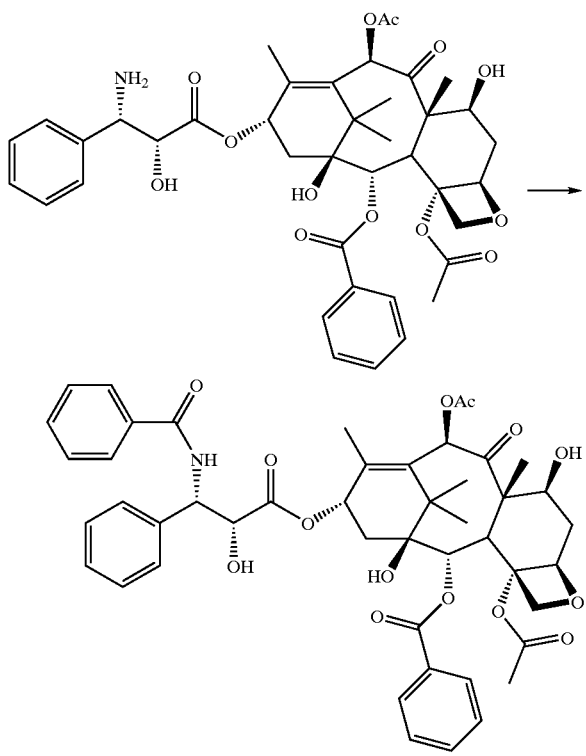

The starting product is 10-deacetyl baccatine III (10-DAB III), which is extracted from the leaves of Taxus baccata. In the first step, 10-DAB III is quantitatively esterified at the C-7 and C-10 hydroxyls. When R=R'=trichloroacetyl, 10-DAB III is reacted with trichloroacetyl chloride in methylene chloride in the presence of triethylamine and of catalytic amounts of 4-dimethylaminopyridine (DMAP). When R≠R', first 10-DAB III is selectively acetylated with acetic anhydride in the presence of cerium, scandium, ytterbium salts, preferably CeCl3.7H20. The resulting baccatine III is subsequently protected at C-7 with a t-butoxycarbonyl or trichloroacetyl group. The first can be introduced by reacting baccatine III with t-butoxy-pyrocarbonate in the presence of DMAP and ethyldiisopropylamine or, alternatively, following the procedure described in U.S. Pat. No. 5,917,062. The trichloracetyl group can be introduced at position 7 by reaction with trichloroacetyl chloride in pyridine.

In the subsequent step (b), the hydroxyl at position 13 is esterified with 3-phenyl-2-epoxypropionic acid, preferably with its ammonium salt in toluene in the presence of dicyclohexylcarbodiimide, DMAP and p-toluenesulfonic acid, thereby obtaining (2R,3R)-3-phenyl-2,3-epoxypropionic acid baccatine III ester.

When both protective groups R and R' are trichloroacetyl, they can be removed using the conditions and reagents described by Zheng et al., Tetrahedron Lett., 1995, 36, 2001, and by Datta et al., J. Org. Chem., 1995, 60, 761. Preferably, the two trichloroacetyl groups are removed with two equivalents of ammonium hydroxide. The deprotected compound is selectively acetylated at position 10 with acetic anhydride in the presence of cerium, scandium or ytterbium salts, preferably CeCl$_3$.7H2O.

The resulting compound is reacted with NaN$_3$ in aqueous methanol in the presence of methyl formate, in the conditions reported in literature (Yamaguchi T., Tetrahedron Letters 39, 5575–78, 1998), to provide the corresponding azide.

Alternatively, when R=trichloroacetyl and R'=acetyl (d), the oxirane reacts with NaN$_3$ to give the corresponding azide with deprotection at the 7-position, corresponding to the compound obtained at step (c').

The azide is reduced to amine in the subsequent step (d). The reduction can be carried out with hydrogen on catalyst or with PPh$_3$. The product obtained at the last step (e) is benzoylated at the amino group to give paclitaxel. Benzoylation can be carried out with benzoic anhydride either simultaneously to reduction or subsequently on the isolated reduced product, using stoichiometric amounts of benzoyl chloride in the presence of potassium carbonate.

The following examples illustrate the invention in greater detail.

EXAMPLE I

Synthesis of 7-Trichloroacetyl-baccatine III

In a 25 ml round-bottom flask, 0.603 g (1.03 mmol, 1.0 eq) of baccatine III were dissolved under magnetic stirring in 9.7 ml of dry pyridine at 25° C. under nitrogen atmosphere. 138 µl (1.23 mmol, 1.23 eq) of trichloroacetyl chloride were dropped into the clear pale yellow solution. 30 min after completion of the addition, a white precipitate formed. Further 120 µl (1.07 mmol; 1 eq) of trichloroacetyl chloride were dropped into the reaction suspension, under the same conditions as above. After 20 min the solution had yellow-brown color. The almost complete conversion of the starting baccatine III was observed by TLC (SiO$_2$, n-hexane/ EtOAc, 2:3). The reaction mixture was diluted with CH$_2$Cl$_2$. The resulting solution was repeatedly washed with a CuSO$_4$ saturated solution, until pyridine had been completely removed (the solution had no longer blue color). The organic phase was concentrated under vacuum, dried over MgSO$_4$, filtered, and the solvent was evaporated, to obtain 0.612 g of a white-yellowish powder corresponding to 7-trichloroacetyl-baccatine III, having the following spectroscopic characteristics.

$^1$H NMR (400 MHz, CDCl$_3$): δ$_{ppm}$=1.08 (s, 3H, Me), 1.13 (s, 3H, Me), 1.86 (s, 3H, Me), 1.97 (ddd, 1H, J$_1$=14.4 Hz, J$_2$=10.3 Hz, J$_3$32 1.9 Hz, C6-H), 2.13 (d, 3H, J=1,2 Hz, Me), 2.15 (s, 3H, Me), 2.30 (s, 3H, Me), 2.32–2.28 (m, 2H, C14-H$_2$), 2.68 (ddd, 1H, J$_1$=14.4 Hz, J$_2$=9.3 Hz, J$_3$=7.3 Hz, C6-H), 4.04 (d, 1H, J=7.0 Hz, C3-H), 4.17-(dd, 1H, J$_1$=8.4 Hz, J$_2$=1.0 Hz, C20-H), 4.34 (d, 1H, J=8.4 Hz, C20-H), 4.86 (t, 1H, J=7.5 Hz, C13-H), 4.98 (dd, 1H, J$_1$=9.5 Hz, J$_2$=1.7 Hz, C5-H), 5.65 (d, 1H, J=7.0 Hz, C2-H), 5.70 (dd, 1H, J$_1$=10.4 Hz, J$_2$=7.4 Hz, C7-H), 6.42 (s, 1H, C10-H), 7.52–7.46 (m, 2H, arom), 7.62 (m, 1H, arom), 8.10 (m, 2H, arom); $^{13}$C NMR (100 MHz, CDCl$_3$): δ$_{ppm}$=10.8, 15.5, 20.4, 20.9, 22.8, 26.9, 32.5, 38.6, 43.0, 47.2, 56.2, 68.1, 74.5, 75.5, 76.5, 77.0, 79.0, 80.5, 83.7, 89.9, 129.0, 129.4, 130.3, 132.0, 134.0, 145.4, 160.8, 167.2, 169.2, 171.0, 201.9.

EXAMPLE II

Synthesis of (2'R,3'R)-7-Trichloroacetyl-baccatine III-13-(3'-phenyl-2',3'-epoxypropionate)

0.164 g (1.00 mmol, 1 eq) of freshly prepared 3-phenyl-2-epoxypropionic acid were dissolved at 0° C. in 30 ml of anhydrous toluene. Subsequently 0.5 g (1 mmol, 0.68 eq) of 7-(trichloroacetyl)-baccatine III [7-(TCA)-baccatine III] were added under nitrogen atmosphere at 0° C. Finally, dicyclohexylcarbodiimide (DCC, 0.21 g, 1.00 mmol, 1.0 eq), 4-dimethylamino pyridine (DMAP, 0.084 g, 0.68 mmol, 0.66 eq) and p-toluenesulfonic acid (p-TSA, 0.17 g, 0.10 mmol, 0.1 eq) were added, in succession. The solution was then heated at 70° C. under magnetic stirring and nitrogen flow. The progress of the reaction was controlled by TLC (SiO$_2$, n-hexane/EtOAc, 3:2). The first spot, having R$_f$=0.28, corresponds to 7-(TCA)-baccatine III epoxy ester. The second spot, having R$_f$=0.11, corresponds to 7-(TCA)-baccatine III. After 3 hours, the mixture was cooled and the suspended solid was filtered. The precipitated dicylohexylurea (DCU) was washed with CH$_2$Cl$_2$. The combined organic fractions were concentrated to dryness. The resulting crude (0.919 g) was chromatographed by flash chromatography (SiO$_2$, n-hexane/EtOAc, 3:2). 0.100 g (0.14 mmol, 20%) of unreacted 7-TCA-baccatine III and 0.435 g (0.49 mmol, 73%) of (2'R,3'R)-7-Trichloroacetyl-baccatine III-13-(3'-phenyl-2',3'-epoxypropionate) having the following spectroscopic characteristics were obtained:

$^1$H NMR (400 MHz, CDCl$_3$): δ$_{ppm}$=1.11 (bs, 6H, 2Me), 1.25 (bs, 1H, OH), 1.76 (d, 3H, J=1.2 Hz, Me), 1.84 (s, 3H, Me), 2.02–1.92 (m, 3H, C14-H$_2$+C6-H), 2.13 (s, 3H, Me), 2.39 (s, 3H, Me), 2.69 (ddd, 1H, J$_1$=14.6 Hz, J$_2$=9.3 Hz, J$_3$=7.3 Hz, C6-H), 3.92 (d, 1H, J=6.9 Hz, C3-H)+, 3.97 (d, 1H, J=4.7 Hz, C2'-H), 4.15 (dd, 1H, J$_1$=8.4 Hz, J$_2$=1.0 Hz, C20-H), 4.31 (d, 1H, J=8.3 Hz, C20-H), 4.33 (d, 1H, J=4.7 Hz, C3'-H), 4.97 (dd, 1H, J$_1$=9.5 Hz, J$_2$=1.8 Hz, C5-H), 5.63 (d, 1H, J=6.8 Hz, C2-H), 5.65 (dd, 1H, J$_1$=10.7 Hz, J$_2$=7.33 Hz, C7-H), 6.02 (dt, 1H, J$_1$32 8.8 Hz, J$_2$=1.8 Hz, C13-H), 7.45–7.30 (m, 5H, arom), 6.34 (s, 1H, C10-H), 7.49 (m, 2H, arom), 7.64 (m, 1H, arom), 8.00 (m, 2H, arom); $^{13}$C NMR (100 MHz, CDCl$_3$): δ$_{ppm}$=10.8, 14.9, 20.8, 21.0, 22.5, 26.5, 32.4, 35.7, 43.2, 46.7, 56.0, 56.1, 57.9, 70.9, 74.5, 74.8, 76.4, 76.7, 79.0, 80.6, 83.6, 89.8, 126.8, 128.7, 128.9, 129.2, 129.3, 130.2, 132.6, 133.0, 134.1, 141.3, 160.7, 166.3, 167.1, 169.1, 170.1, 201.3.

EXAMPLE III

Synthesis of (2'R,3'R)-baccatine III-13-(3'-azido-2'-hydroxy-3'-phenyl-propionate.

In a 25 ml one-necked round-bottom flask equipped with magnetic stirrer, 0.397 g (0.45 mmol, 1 eq) of (2'R,3'R)-7-trichloroacetyl-baccatine III 13-(3'-phenyl-2',3'-epoxypropionate) were suspended at 25° C. in 10.0 ml of CH$_3$OH. 1.26 ml of H$_2$O, 1.26 ml of HCOOCH$_3$ and 0.735 g (11.3 mmol, 25.0 eq) of sodium azide were added in succession. Temperature was raised to 50° C. and the progress of the reaction was checked by TLC (SiO$_2$, CHCl$_3$/EtOAc/MeOH, 12.0:2.0:0.3). Disappearance of the starting product and simultaneous formation of two products having R$_f$=0.22 and 0.29, respectively, were observed. The product having R$_f$=0.29 was subsequently identified as the final product, whereas the product with R$_f$=0.22 was (2'R,3'R)-baccatine III-13-(3'-phenyl-2',3'-epoxypropionate) formed as a reaction intermediate. The product having R$_f$=0.29 growths in time to the detriment of the product having R$_f$=0.22. The reaction solution after 46 h had yellow brown color with a white precipitate (unreacted NaN$_3$). The reaction was quenched after 46 h by addition of water, two further spots were observed, with R$_f$0.38 and 0.13 (unrecovered decomposition products). The precipitated milky white solid was filtered, washed with water and then with AcOEt. A diphasic mixture was obtained, both phases being clear. The two phases were separated. The aqueous phase was extracted three times with AcOEt and the combined organic phases were concentrated and dried over MgSO$_4$. The mixture was filtered and the solvent was evaporated off, to obtain 0.335 g of a white-yellowish powder. The resulting crude was purified by flash chromatography (SiO$_2$, CHCl$_3$/EtOAc/MeOH 12:2:0.3), to obtain 0.279 g (0.36 mmol; 80%; R$_f$0.22) of (2'R,3'R)-baccatine III-13-(3'-azido-2'-hydroxy-3'-phenyl -propionate).

The compound has the following spectroscopic characteristics:

$^1$H NMR (400 MHz, CDCl$_3$): δ$_{ppm}$=1.14 (s, 3H, Me), 1.25 (bs, 4H, Me+OH), 1.67 (s, 3H, Me), 1.87 (ddd, 1H, J$_1$=13.9 Hz, J$_2$=11.1 Hz, J$_3$=2.5 Hz, C6-H), 1.93 (d, 3H, J=0.8 Hz, Me), 2.08 (d, 2H, J=8.8 Hz, C14-H$_2$), 2.24 (s, 3H, Me), 2.26 (s, 3H, Me), 2.55 (m, 2H, C6-H+C7-OH), 3.28 (d, 1H, J=8.4 Hz, C2'-OH), 3.77 (d, 1H, J=7.2 Hz, C3-H), 4.15 (dd, 1H, J$_1$=8.2 Hz, J$_2$=0.8 Hz, C20-H), 4.28 (d, 1H, J=8.2 Hz, C20-H), 4.41 (m, 2H, C7-H+C2'-H) 4.93 (dd, 1H, J$_1$=9.6 Hz, J$_2$=2.0 Hz, C5-H), 4.96 (d, 1H, J=4.4 Hz, C3'-H), 5.64 (d, 1H, J=7.2 Hz, C2-H), 6.17 (dt, 1H, J$_1$=7.9 Hz, J$_2$=1.2 Hz, C13-H), 6.30 (s, 1H, C10-H), 7.46–7.32 (m, 5H, arom), 7.46–7.32 (m, 5H, arom), 7.50 (m, 2H, arom), 7.63 (m, 1H, arom), 8.06 (m, 2H, arom); $^{13}$C NMR (100 MHz, CDCl$_3$): δ$_{ppm}$=9.8, 15.3, 21.1, 21.9, 22.6, 27.0, 35.6, 35.8, 43.3, 45.9, 58.8, 68.1, 72.0, 72.4, 75.1, 75.3, 75.8, 76.7, 79.4, 81.3, 84.6, 127.9, 128.9, 129.2, 129.5, 130.3, 133.4, 134.1, 135.3, 142.2, 167.2, 170.5, 171.5, 203.8.

EXAMPLE IV

Synthesis of N-debenzoyl-paclitaxel

In a 25 ml two-necked round-bottom flask, 0.102 g (0.13 mmol, 1.0 eq) of (2'R,3'R)-7-hydroxy-baccatine III-13(3'-azido-2'-hydroxy-3'-phenyl-propionate) were dissolved in 5.2 ml of freshly distilled CH$_2$Cl$_2$ and the resulting pale yellow solution was added with H$_2$O (0.05 ml), then with 0.071 g (0.26 mmol, 2.0 eq) of PPh$_3$. The mixture was reacted at room temperature under magnetic stirring. After 16 h the reaction was checked by TLC (SiO$_2$, CHCl$_3$/CH$_3$OH 9:1). The starting product (R$_f$=0.61) had disappeared and a spot with R$_f$=0.19 was observed. The reaction was quenched by diluting the mixture (of pale yellow color with white precipitate) with CHCl$_3$. Afterwards, the mixture was washed with distilled H$_2$O and then with a sodium chloride saturated solution (brine). The bright yellow organic phase was dried over MgSO$_4$, then filtered and the solvent was evaporated off. 0.177 g of an ochre yellow oil were obtained. The crude was subjected to flash chromatography (SiO$_2$, CHCl3/CH$_3$OH 9:1), to obtain 0.074 mg (0.10 mmol; 76%) of N-debenzoyl-paclitaxel (pale yellow powder).

$^1$H NMR (400 MHz, CDCl$_3$): δ$_{ppm}$=1.07 (s, 3H, Me), 1.09 (s, 3H, Me), 1.38–1.22 (bs, 2H, 2OH), 1.75 (s, 3H, Me), 1.88 (s, 3H, Me), 1.90 (s, 3H, Me), 1.93 (s, 3H, Me), 2.20–1.96 (m, 6H, C14-H$_2$+C6-H, NH2+OH), 2.52 (ddd, 1H, J$_1$=15.7 Hz, J$_2$=9.5 Hz, J$_3$=5.9 Hz, C6-H), 3.88 (d, 1H, J=7.2 Hz, C3-H), 4.10 (d, 1H, J=4.0 Hz, C20-H), 4.17 (d, 1H, J=4.0 Hz, C20-H), 4.22 (d, 1H, J=8.0 Hz, C2'-H), 4.26 (d, 1H, J=8.0 Hz, C3'-H), 4.56 (dd, 1H, J$_1$=11.6 Hz, J$_2$=6.9 Hz, C7-H), 4.84 (d, 1H, J=8.8 Hz, C5-H), 5.83 (d, 1H, J=7.2 Hz, C2-H), 6.25 (t, 1H, J=8.0 Hz, C13-H), 6.51 (s, 1H, C10-H), 7.20–7.00 (m, 8H, arom), 8.13 (m, 2H, arom); $^{13}$C NMR (100 MHz, CDCl$_3$): δ$_{ppm}$=9.8, 15.2, 21.1, 22.0, 22.7, 27.0, 30.0, 35.4, 35.8, 43.3, 45.9, 58.7, 71.3, 72.3, 75.2, 75.8, 76.6, 79.3, 81.2, 84.6, 127.2, 128.5, 128.9, 129.0, 129.4, 130.3, 133.1, 134.1, 142.6, 167.1, 170.4, 171.5, 173.2, 203.9.

EXAMPLE V

Synthesis of Paclitaxel

In a 10 ml round-bottom flask, 0.031 g (0.041 mmol, 1.0 eq) of N-debenzoyl-paclitaxel were dissolved in 1.25 ml of AcOEt. The clear yellow solution was added with 1.25 ml of a NaHCO$_3$ aqueous saturated solution. 7.1 ml (0.064 mmol, 1.5 eq) of benzoyl chloride were dropped into the resulting diphasic mixture, under strong magnetic stirring. The progress of the reaction was checked by TLC (SiO$_2$, CHCl$_3$/CH$_3$OH 9:1). After disappearance of the starting product, a single spot having R$_f$=0.50 was observed. The reaction mixture was diluted with AcOEt. The organic phase was separated from the aqueous one, which was extracted with AcOEt (three extractions). The combined organic phases were dried over MgSO$_4$, filtered and concentrated. The crude (0.037 g) was dissolved in a 1:1 mixture of CH$_2$Cl$_2$/ethyl ether, then n-pentane (0.030 g, 0.035 mmol, 86%) was added to precipitate paclitaxel, having the spectroscopic characteristics reported in literature.

EXAMPLE VI

Synthesis of the (2'R,3'R)-7,10-bis-trichloroacetyl-10deacetyl-baccatine III-13-(3'-phenyl-1', 3'-epoxypropionate)

In a 100 ml round-bottom flask 0.178 g (1.09 mmol, 1.0 eq) of freshly prepared 3-phenyl-2-epoxypropionic acid at 0° C. were dissolved in 30 ml of anhydrous toluene. In the resulting solution, under nitrogen atmosphere and at 0° C., 0.663 g (0.79 mmol, 0.73 eq) of 7,10-bis-(trichloroacetyl)-10-deacetyl baccatine III [7,10-bis-(TCA)-10-DAB III] were suspended. Finally dicyclohexylcarbodiimide (DCC, 0.224 g, 1.09 mmol, 1.0 eq), 4-dimethylaminopyridine (DMAP, 0.088 g, 0.72 mmol, 0.66 eq) and p-toluenesulfonic acid (p-TSA, 0.19 g, 0.11 mmol, 0.1 eq) were added, in succession. The reaction was carried out in heterogeneous phase at 70° C. under magnetic stirring and nitrogen flow. The progress of the reaction was checked by TLC (SiO$_2$, n-hexane/EtOAc, 3:2). The first spot having R$_f$=0.28 corresponds to 7,10-bis-(TCA)-10-DAB III epoxy ester. The second spot having R$_f$=0.15 corresponds to 7,10-bis-(TCA)-10-DAB III. After 3 hours the mixture was cooled and the suspended solid was filtered. The dark yellow precipitate was washed with CH$_2$Cl$_2$: the residual white solid was DCU. The combined organic fractions were concentrated and the resulting solid was subjected to flash chromatography (SiO$_2$, n-hexane/EtOAc, 3:2). 0.63 g of (2'R,3'R)-7,10-bis-trichloroacetyl-10-deacetyl-baccatine III-13–3'-phenyl-2',3'-epoxypropionate were obtained.

$^1$H NMR (400 MHz, CDCl$_3$): δ$_{ppm}$=1.12 (s, 3H, Me), 1.14 (s, 3H, Me), 1.76–1.60 (m, 2H, C6-H+OH), 1.81 (s, 3H, Me), 1.88 (s, 3H, Me), 2.04–1.98 (m, 2H, C14-H), 2.41 (s, 3H, Me), 2.69 (ddd, 1H, J$_1$=14.5 Hz, J$_2$=9.3 Hz, J$_3$=7.3 Hz, C6-H), 3.89 (d, 1H, J=7.2 Hz, C3-H), 3.98 (d, 1H, J=4.0 Hz, C2'-H), 4.14 (d, 1H, J=8.0 Hz, C20-H), 4.32 (d, 1H, J=8.0 Hz, C20-H), 4.34 (d, 1H, J=4.0 Hz, C3'-H), 4.97 (d, 1H, J=7.6 Hz, C5-H), 5.70–5.62 (m, 2H, C7-H+C2-H), 6.05 (dt, 1H, J$_1$=8.4 Hz, J$_2$=1.0Hz, C13-H), 7.52–7.30 (m, 7H, ArH), 6.39 (s, 1H, C10-H), 7.45 (m, 1H, ArH) 7.99 (m, 2H, ArH); $^{13}$C NMR (100 MHz, CDCl$_3$): δ$_{ppm}$=10.9, 15.1, 20.8, 22.6, 26.3, 32.5, 35.6, 43.1, 46.7, 55.9, 56.5, 58.0, 70.8, 74.2, 76.4, 78.6, 78.9, 80.5, 83.5, 89.5, 89.6, 126.8, 128.8, 129.0, 129.1, 129.4, 130.2, 131.5, 132.5, 134.2, 143.3, 160.6, 161.1, 166.3, 167.0, 170.3, 199.5.

EXAMPLE VII

Synthesis of (2'R,3'R)-10-deacetyl-baccatine III-13 (3'-phenyl-2',3'-epoxypropionate)

In a 25 ml round-bottom flask, 0.174 g (0.18 mmol, 1.0 eq) of (2'R,3'R)-7,10-bis(TCA)-10-DAB III-13-(3'-phenyl-2',3'-epoxypropionate) were suspended in 3 ml of CH$_3$OH. The resulting suspension was cooled to 0° C. and 0.24 ml (0.36 mmol, 2.0 eq) of a 1.57 M NH$_3$ aqueous solution were dropped therein, under strong magnetic stirring. The reaction was carried out for 15 min at 0° C., during which the suspension became yellow-greenish. After that, the mixture was warmed to room temperature and reacted for a further 5 min, to completely dissolve the precipitate, obtaining a clear yellow-greenish solution. The complete disappearance of the starting compounds was checked by TLC (SiO$_2$, n-hexane/EtOAc, 3:2), which gave a single spot on the baseline. The reaction mixture was diluted with H$_2$O to obtain a milky white solution, the organic phase was extracted therefrom (3 extractions) with AcOEt (upon addition of the organic solvent, an emulsion formed which was broken by dissolving NaCl therein). The combined organic phases were dried over MgSO$_4$, filtered, and the solvent was evaporated. 0.194 g of white powder of (2'R,3'R)-10-deacetyl-baccatine III-13-(3'-phenyl-2',3'-epoxypropionate) were obtained.

$^1$H NMR (400 MHz, CDCl$_3$): δ$_{ppm}$=1.05 (s, 3H, Me), 1.09 (s, 3H, Me), 1.71 (s, 3H, Me), 1.72 (d, 3H, J=1.2 Hz, Me), 1.83 (m, 1H, C6-H), 1.95 (2H, d, J=8.8 Hz, C14-H$_2$), 2.34 (s, 3H, Me), 2.58 (ddd, 1H, J$_1$=14.6 Hz, J$_2$=9.9 Hz, J$_3$=6.9 Hz, C6-H), 3.85 (d, 1H, J=7.3 Hz, C3-H), 3.95 (d, 1H, J=4.4 Hz, C2'-H), 4.14 (d, 1H, J=8.4 Hz, C20-H), 4.22 (dd, 1H, J$_1$=11.3 Hz, J$_2$=6.6 Hz, C7-H), 4.27 (d, 1H, J=8.4 Hz, C20-H), 4.31 (d, 1H, J=4.4 Hz, C3'-H), 4.95 (d, 1H, J=8.8 Hz, C5-H), 5.16 (s, 1H, C10-H), 5.59 (d, 1H, J=7.3 Hz, C3-H), 5.99 (dt, 1H, (d, 1H, J$_1$=8.8 Hz, J$_2$=1.2 Hz, C7-H), 7.30–7.50 (m, 7H, arom), 7.60–7.70 (m, 1H, arom), 7.90–8.00 (m, 2H, arom).

EXAMPLE VIII

Synthesis of (2'R,3'R)-baccatine III-13-(3'-phenyl2', 3'-epoxypropionate)

A solution of (2'R,3'R)-10-deacetyl-baccatine III-13-(3'-phenyl-2',3'-epoxypropionate) (138 mg) in 3 ml of dry tetrahydrofuran was added with 7.3 mg of CeCl$_3$.7H$_2$O and 0.073 ml of acetic anhydride. The reaction mixture was stirred at room temperature for 5 hours, during which time the reaction mixture became homogeneous. 1 g of ice was added, keeping under stirring for 1 hour. The organic solvent was evaporated off under vacuum and the residue was diluted with 5 ml of H$_2$O. The formed precipitate was filtered and dried under vacuum pump for 18 h. The resulting product (white powder, 130 mg) has the following characteristics:

$^1$H NMR (400 MHz, CDCl$_3$): δ$_{ppm}$=1.05 (s, 3H, Me), 1.09 (s, 3H, Me), 1.71 (s, 3H, Me), 1.72 (d, 3H, J=1.2 Hz, Me), 1.83 (m, 1H, C6-H), 1.95 (2H, d, J=8.8 Hz, C14-H$_2$), 2.34 (s, 3H, Me), 2.58 (ddd, 1H, J$_1$=14.6 Hz, J$_2$=9.9 Hz, J$_3$=6.9 Hz, C6-H), 3.85 (d, 1H, J=7.3 Hz, C3-H), 3.95 (d, 1H, J=4.4 Hz, C2'-H), 4.14 (d, 1H, J=8.4 Hz, C20-H), 4.22 (dd, 1H, J$_1$=11.3 Hz, J$_2$=6.6 Hz, C7-H), 4.27 (d, 1H, J=8.4 Hz, C20-H), 4.31 (d, 1H, J=4.4 Hz, C3'-H), 4.95 (d, 1H, J=8.8 Hz, C5-H), 5.59 (d, 1H, J=7.3 Hz, C3-H), 5.65 (dd, 1H, J$_1$=10.7 Hz, J$_2$=7.33 Hz, C7-H), 6.34 (s, 1H, C10-H), 7.30–7.50 (m, 7H, arom), 7.60–7.70 (m, 1H, arom), 7.90–8.00 (m, 2H, arom).

EXAMPLE IX

Synthesis of (2'R,3'R)-baccatine III-13-(3'-azido-2'-hydroxy-3'-phenyl-propionate.

In a 25 ml one-necked round-bottom flask equipped with magnetic stirring, 0.17 g (0.45 mmol, 1 eq) of (2'R,3'R)

baccatine III 13-(3'-phenyl-2',3'were suspended at 25° C. in 5 ml of CH₃OH. 0.63 ml of H₂O, 0.23 ml of HCOOCH₃ and 0.36 g (5.5 mmol, 12.5 eq) of sodium azide were added in succession. The mixture was heated to 50° C. and the progress of the reaction was checked by TLC (SiO₂, CHCl₃/EtOAc/MeOH, 12.0:2.0:0.3). The reaction mixture after 46 h had yellow brown color with a white precipitate (unreacted NaN₃). H₂O (10 ml) was added and the precipitated milky white solid was filtered, washed with water and then with AcOEt. The two phases were separated, the aqueous phase was extracted three times with AcOEt and the combined organic phases were concentrated and dried over MgSO₄, filtered and the solvent was evaporated off, to obtain 0.20 g of a white-yellowish powder. The resulting crude was purified by flash chromatography (SiO₂, CHCl₃/EtOAc/MeOH 12:2:0.3), to obtain 0.140 g of (2'R,3'R)-baccatine III-13-(3'-azido-2'-hydroxy-3'-phenyl-propionate).

The compound has the same spectroscopic characteristics as the compound obtained in Example III.

What is claimed is:

1. A process for the preparation of paclitaxel, which comprises the following steps:

a) protection of the hydroxyls at the 7- and 10-positions of 10-deacetylbaccatine III (10-DAB III), wherein -R=R'-trichloracetyl, or R'=-acetyl and R is selected from t-butoxycarbonyl and trichloracetyl, b) esterification of the hydroxyl at the 13-position with 3-phenyl-2-epoxypropionic acid

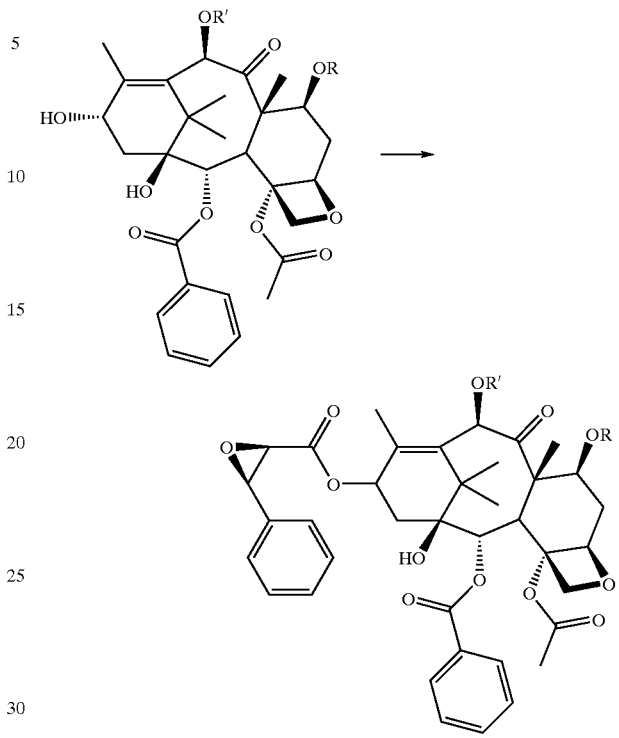

c) removal of the protective groups at 7 and 10 (1) if they are both trichloroacetyl groups, followed by selective acetylation at the 10-position (2) and opening of the epoxide with sodium azide (3);

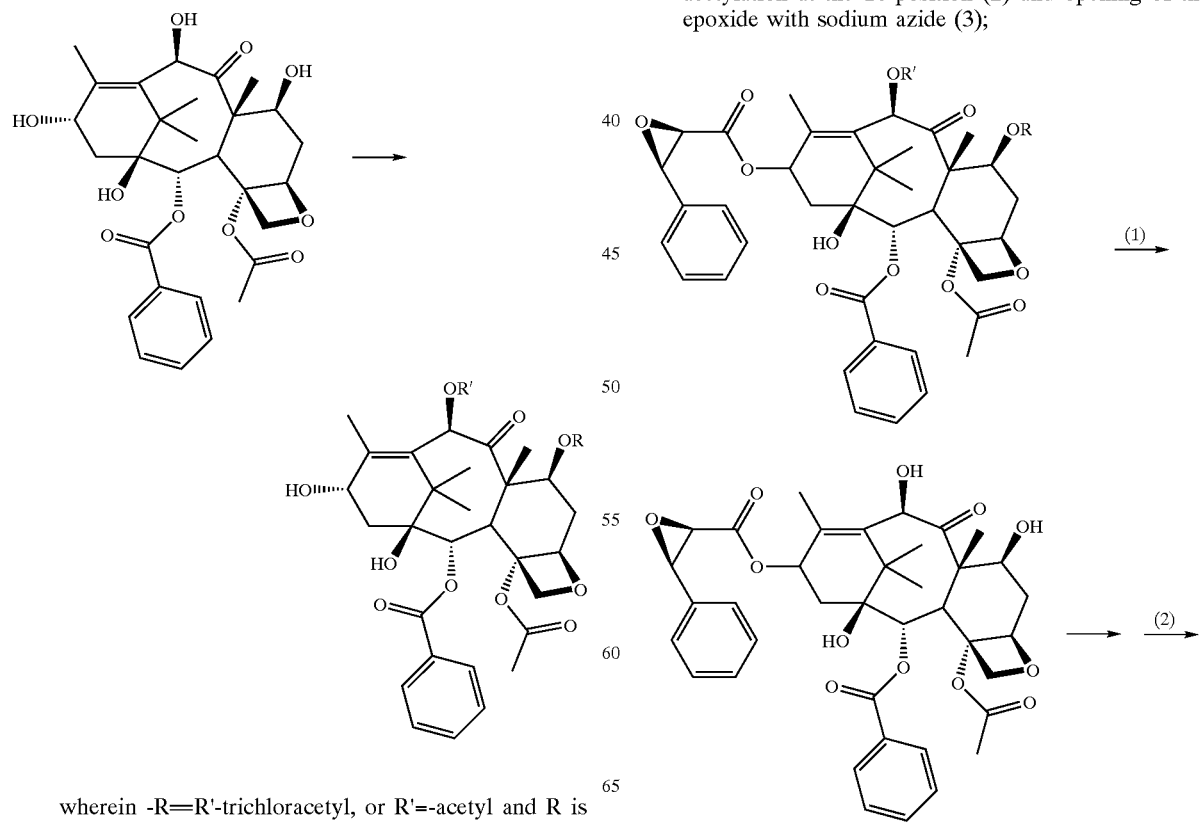

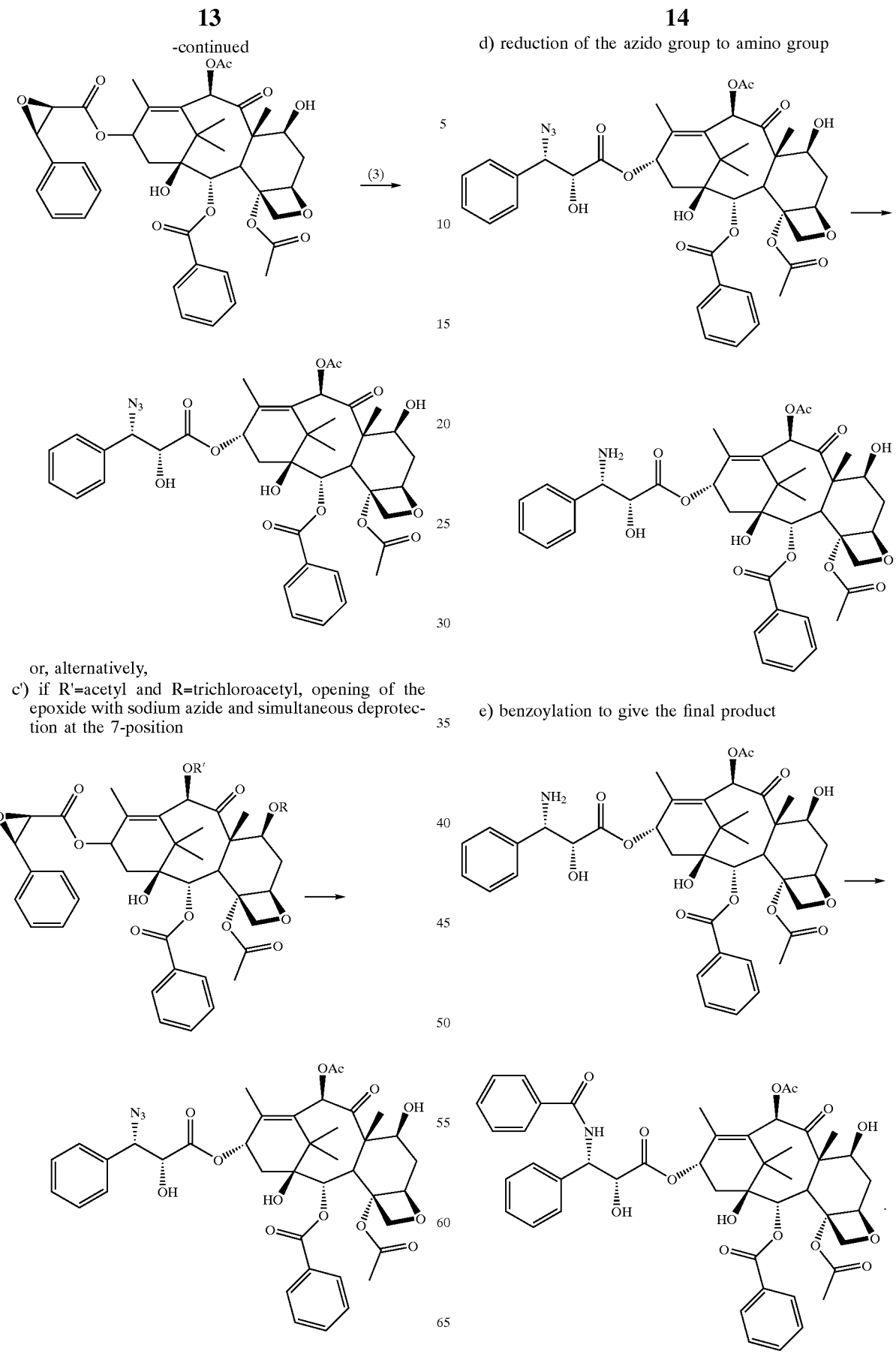
or, alternatively,
c') if R'=acetyl and R=trichloroacetyl, opening of the epoxide with sodium azide and simultaneous deprotection at the 7-position
d) reduction of the azido group to amino group
e) benzoylation to give the final product 2. A process as claimed in claim 1, wherein 10-DAB III is protected at the 7- and 10-positions with a trichloroacetyl group by reaction with trichloroacetyl chloride in methylene chloride in the presence of triethylamine and catalytic amounts of 4-dimethylaminopyridine (DMAP).

3. A process as claimed in claim 1, wherein 10-DAB III is first acetylated at the 10-position by reaction with acetic anhydride in the presence of cerium, scandium or ytterbium salts, and is subsequently protected at the hydroxyl at 7- with a t-butoxycarbonyl or trichloroacetyl group.

4. A process as claimed in claim 1, wherein the hydroxyl at 13- is esterified with phenyl-2-epoxypropionic acid ammonium salt in toluene in the presence of dicyclohexylcarbodiimide (DCC), DMAP and p-toluenesulfonic acid.

5. A process as claimed in claim 1, wherein the protective groups R=R'-trichloroacetyl are removed with ammonium hydroxide.

6. A process as claimed in claim 1, wherein the epoxide is opened with $NaN_3$ in aqueous methanol in the presence of methyl formate.

7. A process as claimed in claim 1, wherein the azide is reduced to amine with hydrogen on catalyst or with $PPh_3$.

8. A process as claimed in claim 1, wherein benzoylation at the last step is carried out with benzoic anhydride either simultaneously to reduction or subsequently on the isolated reduced product with benzoyl chloride in the presence of potassium carbonate.

9. As reaction intermediates, the following compounds:

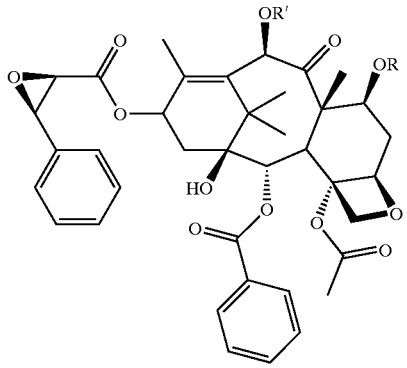

wherein R and R' are as defined in claim 1 or hydrogen.

* * * * *